United States Patent [19]

Deason et al.

[11] 4,035,372

[45] July 12, 1977

[54] 4-{[4-(DIPHENYLMETHYL)-1-PIPERIDINYL]METHYL}BENZENAMINES

[75] Inventors: James R. Deason; Robert W. Hamilton, both of Wilmette; Harman S. Lowrie; Kurt J. Rorig, both of Glenview, all of Ill.

[73] Assignee: G. D. Searle & Co., Chicago, Ill.

[21] Appl. No.: 714,429

[22] Filed: Aug. 13, 1976

[51] Int. Cl.[2] .................................... C07D 211/14
[52] U.S. Cl. .................. 260/293.77; 260/293.79; 424/267
[58] Field of Search ................. 260/293.77, 293.79

[56] References Cited

U.S. PATENT DOCUMENTS

| | | | |
|---|---|---|---|
| 3,068,237 | 12/1962 | Rorig | 260/293.79 |
| 3,759,928 | 9/1973 | Zivkovic | 260/293.79 |
| 3,946,022 | 3/1976 | Carr et al. | 260/293.79 |

Primary Examiner—Norma S. Milestone
Attorney, Agent, or Firm—John M. Brown

[57] ABSTRACT

4-{[4-(Diphenylmethyl)-1-piperidinyl]methyl}benzenamines useful by reason of their vasodilating activity are disclosed.

6 Claims, No Drawings

4-{[4-(DIPHENYLMETHYL)-1-PIPERIDINYL]METHYL}BENZENAMINES

This invention relates to 4{[4-(diphenylmethyl)-1-piperidinyl]methyl}benzenamines and processes for the preparations thereof. More particularly, this invention provides new, useful, and unobvious chemical compounds of the formula

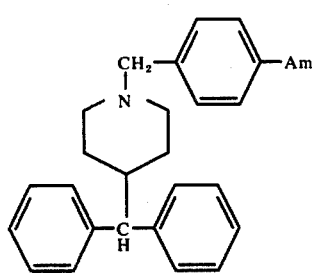

wherein Am represents an amino, alkanoylamino, alkylamino, or dialkylamino radical.

Among the alkanoylamino radicals represented by Am in the foregoing formula, especially lower alkanoylamino radicals are preferred, which is to say radicals of the formula

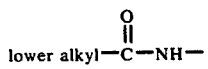

wherein the lower alkyl grouping is methyl, ethyl, 1-methylethyl, 1,1-dimethylethyl, propyl, 1-methylpropyl, 2-methylpropyl, 2,2-dimethylpropyl, butyl, pentyl, 4-methylpentyl, hexyl, 3-methylhexyl, heptyl, or like monovalent, saturated, acyclic, straight- or branched-chain, hydrocarbon moiety of the formula $$-C_nH_{2n+1}$$

in which n represents a positive integer less than 8.

The alkyl constituents of the alkylamino and dialkylamino radicals represented by Am in the introductory formula likewise are preferably of lower order, comprising thus in each instance fewer than 8 carbons.

Equivalent to the basic amines hereinbefore enformulated, for the purposes of this invention, are non-toxic acid addition salts thereof having the formula

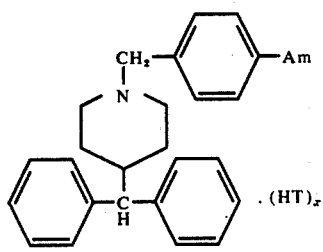

wherein T represents one equivalent of an anion — for example, chloride, bromide, iodide, nitrate, phosphate, sulfate, sulfamate, methyl sulfate, ethyl sulfate, benzenesulfonate, toluenesulfonate, acetate, lactate, succinate, maleate, tartrate, citrate, gluconate, ascorbate, benzoate, cinnamate, or the like — which, in combination with the cationic portion of the salt aforesaid, is neither biologically nor otherwise incompatible and x represents a positive integer less than 3.

The compounds to which this invention relates are useful by reason of their valuable biological properties. For example, they are vasodilators: they dilate blood vessels, thereby decreasing resistance to blood flow and increasing the volume thereof. The potency of the compounds of this invention as vasodilators — and the duration of their activity — is unexpected in view of the low order of such activity — and comparatively short time during which it abides — in prior art compounds represented by N-(4-aminobenzyl)-α,α-diphenyl-4-piperidinemethanol dihydrochloride, U.S. Pat. No. 3,068,237.

The vasodilating activity of the instant compounds can be demonstrated via a standardized test for their capacity to decrease vascular resistance in the peripheral arterial system of a perfused denervated canine hind limb preparation modeled after that described by Botton et al., in J. Pharmacol. Exp. Therap., 152, 243 (1966). By measuring changes in perfusion pressures induced by the compounds under conditions of constant flow, their effects on vascular resistance can be calculated from the relationship resistance = pressure ÷ flow Since denervation eliminates autonomic influence, decreases in pressure are solely attributable to direct vasodilator effect. Because both the intensity of this effect and how long it lasts are pharmacologically important, these parameters are conveniently combined in a so-called Vasodilator Index, which is the product of the maximum decrease in perfusion pressure expressed as a decimal and its duration in seconds. Likewise pharamcologically important is the intensity and duration of increases in vascular resistance which sometimes eventuate, signifying secondary vasoconstriction.

Perfusion preparation is initiated by anesthetizing a random-source mongrel dog of either sex with a mixture of 15 mg/kg of sodium pentobarbital and 300 mg/kg of sodium barbital, administered intravenously. A polyethylene catheter is placed in the right common carotid artery and connected to a miniature pressure transducer whereby systemic arterial pressure is monitored. The sciatic nerve is exposed and sectioned; and the right femoral artery, nerve, and vein are exposed and stripped of perivascular tissue. The femoral nerve is sectioned, thereby denervating the hind limb. A Teflon-coated balloon catheter is proximally placed in the femoral artery near the illiac artery, whereupon the balloon is inflated to prevent perfusion of the deep femoral artery; and the catheter is connected via flexible tubing and a roller pump to a damping chamber adapted to eliminate pulsatile flow from the pump. A polyethylene catheter is distally placed in the femoral artery and connected via a second length of tubing to the damping chamber, completing the perfusion circuit. Pressure within the circuit is monitored by means of a second miniature pressure transducer connected to a T-tube which is inserted between the damping chamber and the distally-emplaced catheter. Finally, an access port is inserted into the circuit distal to the second transducer.

The perfusion circuit is filled via the access port with physiological saline containing 1 mg/ml of heparin; and shortly before perfusion is begun, the test animal is intravenously injected with 300 units/kg of heparin. Collateral vessels are occluded by tightening 2 plastic bands about each side of the hind limb, taking care to ensure that the femoral artery and vein are not constricted. Adequacy of vascular isolation is confirmed by the absence of pulsatile pressure in the perfusion circuit when the pump is stopped. The test is begun by slowly increasing pump output until the perfusion pressure is equal to systemic pressure, whereupon compound is introduced via the access port and pump output is maintained at the original level until the test is completed.

Each compound is tested at 10, 20, and 30 μg/kg, using 0.1 ml of distilled water as the vehicle in each instance. If a 40-μg/kg dose is administered, the volume of the vehicle is increased to 0.12 ml. Each dose of each compound is twice repeated in the same hind limb preparation, a minimum of three preparations being employed. Controls for 10, 20, and 30 μg/kg compound dosages are provided by thrice administering 0.1 ml of distilled water (only) via the access port in each preparation, compound and control administrations being haphazardly interspersed. Like administration of 0.12 ml of distilled water provides controls for a 40 μg/kg dose.

The results of testing N-(4-aminobenzyl)-α,α-diphenyl-4-piperidinemethanol dihydrochloride, identified as SC-30883, and the least remote compound of this invention, the product of Example 1C — 4-{[4-(diphenylmethyl)-1-piperidinyl]methyl}benzenamine dihydrochloride — identified as SC-30394, are summarized in Table I. The numerical characterizations in columns 2-7 thereof are individually derived from the experimental data by first calculating the mean value for the indicated parameter in each preparation and then averaging the results (± standard error). Analysis of the results via Student's t-test indicated that whereas SC-30883 had no effect on vascular resistance, SC-30394 (1) produced a dose-related decrease in resistance for appreciable periods of time, giving rise to elevated Vasodilator Indices; (2) was wholly ineffective only at the lowest dose (10 μg/kg) administered; and (3) did not increase resistance.

TABLE I

| (1) Compound/ Control | (2) Initial Peripheral Resistance (mm of Hg/ ml/min.) | (3) Maximum % Decrease in Peripheral Resistance | (4) Duration of Decreased Resistance (sec.) | (5) Vasodilator Index | (6) Maximum % Increase in Peripheral Resistance | (7) Duration of Increased Resistance (sec.) | (8) N'/N* |
|---|---|---|---|---|---|---|---|
| SC-30394 | | | | | | | |
| 10 μg/kg | 1.28 ± .24 | 13.4 ± 2.4 | 100 ± 10 | 16.1 ± 4.4 | 4.0 ± 2.2 | 124 ± 16 | 2/3 |
| 20 μg/kg | 1.29 ± .25 | 15.5 ± 3.4 | 124 ± 21+ | 19.9 ± 4.4+ | — | — | 0/3 |
| 30 μg/kg | 1.29 ± .22 | 18.9 ± 2.1+ | 128 ± 13+ | 26.1 ± 4.7+ | 4.1 ± 2.3 | 148 ± 28 | 1/3 |
| 40 μg/kg | 1.29 ± .21 | 22.6 ± 3.2+ | 177 ± 25+ | 42.1 ± 11+ | — | — | 0/3 |
| SC-30883 | | | | | | | |
| 10 μg/kg | 1.24 ± .21 | 7.3 ± .5 | 50 ± 14 | 3.9 ± 1.0 | 7.9 ± 1.7 | 151 ± 18 | 2/3 |
| 20 μg/kg | 1.26 ± .22 | 8.9 ± 1.2 | 60 ± 17 | 5.6 ± 1.3 | 7.0 ± 2.1 | 141 ± 33 | 3/3 |
| 30 μg/kg | 1.27 ± .22 | 10.9 ± 2.3 | 71 ± 27 | 7.9 ± 2.8 | 11.0 ± 2.5 | 193 ± 37 | 2/3 |
| 40 μg/kg | 1.29 ± .22 | 14.7 ± 2.5 | 83 ± 33 | 12.1 ± 4.2 | 12.7 ± 1.8 | 224 ± 21 | 2/3 |
| Controls | | | | | | | |
| .10 ml | 1.28 ± .20 | 8.1 ± .8 | 72 ± 8 | 6.4 ± 1.6 | — | — | 0/3 |
| .12 ml | 1.32 ± .24 | 14.0 ± 2.2 | 91 ± 13 | 13.3 ± 3.1 | — | — | 0/3 |

*N' = number of preparations in which a secondary increase in resistance was observed;
N = total number of preparations
+ Significantly different from appropriate control (Student's t, P < .05)

Results of testing the well-known peripheral dilator, papaverine hydrochloride, by the foregoing procedure are summarized in Table II.

TABLE II

| Compound/ Control | Initial Peripheral Resistance (mm of Hg/ ml/min.) | Maximum % Decrease in Peripheral Resistance | Duration of Descreased Resistance (sec.) | Vasodilator Index | Maximum % Increase in Peripheral Resistance | Duration of Increased Resistance (sec.) | N'/N* |
|---|---|---|---|---|---|---|---|
| Papaverine HCl | | | | | | | |
| 10 μg/kg | 1.27 ± .54 | 18.8 ± .5+ | 97.0 ± 37 | 18.0 ± 6.5 | 4.1 | 160 | 1/3 |
| 20 μg/kg | 1.15 ± .29 | 16.7 ± 1.7+ | 8 ± 12 | 148 ± 2.5+ | 3.1 | 84 | 1/3 |
| 30 μg/kg | 1.15 ± .27 | 17.1 ± 3.3+ | 121 ± 10 | 21.2 ± 5.4 | 2.8/160 | 1/4 | |
| Control | | | | | | | |
| .10 ml | .91 ± .06 | 6.1 ± .2 | 84 ± 16 | 5.1 ± .8 | — | — | 0/3 |

*N' = number of preparations in which a secondary increase in resistance was observed;
N = total number of preparations
+ significantly different from control (Student's t, P < .05)

The vasodilating activity of 4-{[4-diphenylmethyl)-1-piperidinyl]methyl}benzenamine dihydrochloride in the foregoing test is specified merely for the purpose of illustration, and is accordingly not to be construed as either delimiting or exclusionary.

Those skilled in the art will recognize that observations of activity in standardized tests for particular biological effects are fundamental to the development of valuable new drugs, both veterinary and human.

For therapeutic purposes, the compounds of this invention are administered in dosage unit form including, but not necessarily limited to, sterile aqueous solutions for intravenous infusion, sterile solutions or suspensions for intramuscular injection or nasal instillation, tablets or capsules or admixtures with liquid for oral ingestion, intravaginal or rectal compositions such as suppositories, lozenges for sublingual use, and salves or lotions (including sprayable solutions or mixtures) for topical application. The preparation of such dosage units, which commonly involves incorporation of one or more adjuvants appropriate to the contemplated route of administration, is well-known in the art. See, for example, Remington's Pharmaceutical Sciences, 15th ed., Arthur Osol et al., Mack Pub. Co., Easton (Pa.) 1975, Parts 2 and 8 in particular. As also is well-known in the art, effective dosage for any therapeutic purpose depends upon the nature of the disease to be treated and its severity, the route of administration, the species of animal involved and its size and individual idiosyncrasies, the specific compound employed, etc.

The basic primary amine of this invention can be prepared by heating 4-(diphenylmethyl)piperidine with 4-nitrobenzyl chloride in the presence of sodium carbonate, using ethanol and water as solvents, and contacting the resultant 1-[(4-nitrophenyl)methyl]-4-(diphenylmethyl)piperidine in tetrahydrofuran solution at 25° with hydrogen under approximately 0.1 atm of pressure, using 5% palladium-on-charcoal as catalyst. From 4-{[4-(diphenylmethyl)-1-piperidinyl]methyl}benzenamine thus or otherwise produced, on heating in acetic acid solution with an alkanoic acid anhydride, a corresponding basic N-alkanoyl amine of this invention can be prepared. And by heating a dichloromethane solution of 4-(diphenylmethyl)piperidine and 4-[(alkylamino)/(dialkylamino)]benzoic acid in the presence of N,N¹-methanetetraylbiscyclohexanamine, then heating the resultant amide with lithium tetrahydroaluminate(1-) in tetrahydrofuran, a corresponding basic N-alkyl or N,N-dialkyl amine of this invention can be prepared.

Contacting a basic amine of this invention with 1 or 2 equivalents of any of various inorganic and strong organic acids in which the anoinic portion can be represented by T as hereinabove defined affords a corresponding equivalent acid addition salt thereof.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees centigrade and relative amounts of materials in parts by weight, except as otherwise noted.

EXAMPLE 1

A. To a solution of 126 parts of 4-(diphenylmethyl)-piperidine in 1200 parts of 95% ethanol is added a solution of 69 parts of sodium carbonate in 1500 parts of water. The resultant mixture is heated at the boiling point under reflux with vigorous stirring while a solution of 112 parts of 4-nitrobenzyl chloride in 800 parts of 95% ethanol is rapidly stirred in, and for 4 hours thereafter. Solvent is then removed by vacuum distillation, and the residue is partitioned between dichloromethane and water. The organic layer is separated, dried over anhydrous potassium carbonate, and stripped of solvent by vacuum distillation. The residue, recrystallized from anhydrous ethanol, affords 1-[(4-nitrophenyl)methyl]-4-(diphenylmethyl)piperidine melting at approximately 130°–131°.

B. A solution of 20 parts of 1-[(4-nitrophenyl)-methyl]-4-(diphenylmethyl)piperidine in approximately 180 parts of tetrahydrofuran is hydrogenated at approximately 0.1 atm and 25° in the presence of 1 part of 5% palladium-on-charcoal for 2 and ½ hours. The catalyst is thereupon filtered out, and the filtrate is stripped of solvent by vacuum distillation. The residue is 4-{[4-(diphenylmethyl)-1-piperidinyl]methyl}benzenamine.

C. To a solution of 5 parts of 4-{[4-(diphenylmethyl)-1-piperidinyl]methyl}benzenamine in 40 parts of methanol is added 4 parts of a 30% solution of hydrogen chloride in 2-propanol, whereupon just sufficient anhydrous ether is introduced to induce precipitation. The precipitate is filtered off and recrystallized from a mixture of methanol and ether to give 4-{[4-(diphenylmethyl)-1-piperidinyl]methyl}benzenamine dihydrochloride melting at 233°–237° with gas evolution. The product has the formula

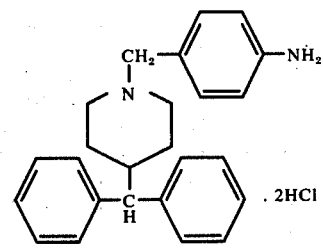

EXAMPLE 2

To a solution of 8 parts of 4-{[4-(diphenylmethyl)-1-piperidinyl]methyl}benzenamine in 50 parts of acetic acid is added 5 parts of acetic anhydride. The resultant mixture is heated to the boiling point under reflux and maintained thereat for 10 minutes, then stripped of solvents by vacuum distillation. The residue is combined with 10 volumes of water. The resultant mixture is made alkaline with concentrated ammonium hydroxide. The mixture thus obtained is extracted with dichloromethane. The dichloromethane extract is dried over anhydrous potassium carbonate and then stripped of solvent by vacuum distillation. The residue, recrystallized from benzene, affords N-acetyl-4-{[4-(diphenylmethyl)-1-piperidinyl]methyl}benzenamine melting at approximately 182°–183°. The product has the formula

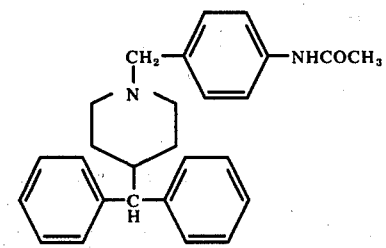

EXAMPLE 3

Substitution of 6 parts of propionic anhydride for the acetic anhydride called for in Example 2 affords, by the procedure there detailed, N-(2,2-dimethyl-1-oxopropyl)-4-{[4-(diphenylmethyl)-1-piperidinyl]methyl}benzenamine.

EXAMPLE 4

A. To a solution of 150 parts of 4-(diphenylmethyl)-piperidine and 99 parts of 4-(dimethylamino)benzoic acid in 4000 parts of dichloromethane is added a solution of 123 parts of N,N¹-methanetetraylbiscyclohexanamine in 1330 parts of dichloromethane. The resultant mixture is stirred for 6 hours, whereupon a further 25 parts of 4-(dimethylamino)benzoic acid and 30 parts of N,N¹-methanetetraylbiscyclohexanamine is introduced and stirring continued thereafter for 24 hours. The reaction mixture is then filtered, and the filtrate is stripped of solvent by vacuum distillation. The residue is taken up in ether; and the ether solution is consecutively washed with 5% hydrochloric acid, water, and 5% ammonium hydroxide, then dried over anhydrous potassium carbonate and finally stripped of solvent by vacuum distillation. The residue is recrystallized from a mixture of benzene and hexane to give 1-[4-(dimethylamino)benzoyl]-4-(diphenylmethyl)-piperidine melting at 177°–179°.

B. To a suspension of 15 parts of lithium tetrahydroaluminate(1-) in 1350 parts of tetrahydrofuran is slowly added a solution of 80 parts of 1-[4-(dimethylamino)benzoyl]-4-(diphenylmethyl)piperidine in 450 parts of tetrahydrofuran. The resultant mixture is heated at the boiling point under reflux for 16 hours, whereupon 16 parts of water, 12 parts of aqueous 20% sodium hydroxide and 56 parts of water are consecutively introduced. Insoluble solids are filtered out, and the filtrate is stripped of solvent by vacuum distillation. The residue is N,N-dimethyl-4-{[4-(diphenylmethyl)-1-piperidinyl]-methyl}benzenamine.

C. To a solution of 80 parts of N,N-dimethyl-4-{[4-(diphenylmethyl)-1-piperidinyl]methyl}benzenamine in 1000 parts of ethanol is added a solution of 16 parts of hydrogen chloride in 40 parts of 2-propanol. Just sufficient water is thereupon introduced to dissolve the precipitate which forms, whereupon anhydrous ether is added q.s. turbidity. The precipitate which forms on standing is isolated by filtration and dried in air. The product thus obtained is N,N-dimethyl-4-{[4-(diphenylmethyl)-1-piperidinyl]methyl}benzenamine dihydrochloride melting at 236°–238° with gas evolution. The product has the formula

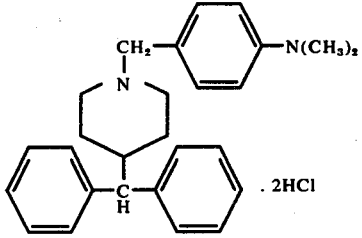

EXAMPLE 5

A. Substitution of 134 parts of 4-[bis(1-methylethyl)amino]benzoic acid for the 4-(dimethylamino)-benzoic acid called for in Example 4A affords, by the procedure there detailed, 1{4-[bis(1-methylethyl)amino]-benzoyl}-4-(diphenylmethyl)piperidine.

B. Substitution of 91 parts of 1-{4-[bis(1-methylethyl)amino]benzoyl}-4-(diphenylmethyl)piperidine for the 1-[4-(dimethylamino)benzoyl]-4-(diphenylmethyl)-piperidine called for in Example 4B affords, by the procedure there detailed, N,N-bis(1-methylethyl)-4-{[4-(diphenylmethyl)-1-piperidinyl]methyl}benzenamine.

C. Substitution of 91 parts of N,N-bis(1-methylethyl)-4-{[4-(diphenylmethyl)-1-piperidinyl]-methyl-}benzenamine for the N,N-dimethyl-4-{[4-(diphenylmethyl)-1-piperidinyl]methyl}benzenamine called for in Example 4C affords, by the procedure there detailed, N,N-bis(1-methylethyl)-4-{[4-(diphenylmethyl)-1-piperidinyl]-methyl}benzenamine dihydrochloride. The product has the formula

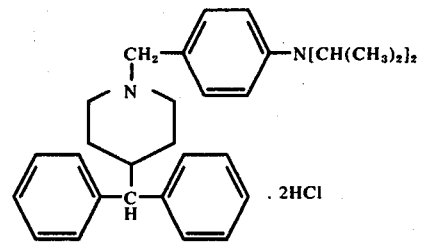

What is claimed is:

1. A compound of the formula

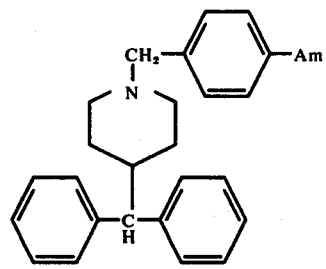

in which Am represents $-NH_2$, $-NHCOC_nH_{2n+1}$, or $-N(C_nH_{2n+1})_2$ wherein $n$ represents a positive integer less than 8.

2. A compound according to claim 1 which is 4-{[4-(diphenylmethyl)-1-piperidinyl]methyl}benzenamine.

3. A compound according to claim 1 having the formula

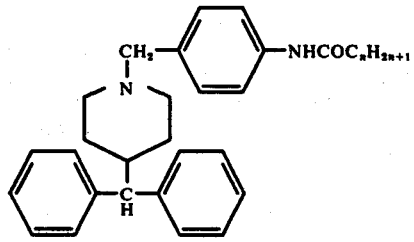

wherein $n$ represents a positive integer less than 8.

4. A compound according to claim 1 which is N-acetyl-4-{[4-(diphenylmethyl)-1-piperidinyl]methyl}-benzenamine.

5. A compound according to claim 1 having the formula

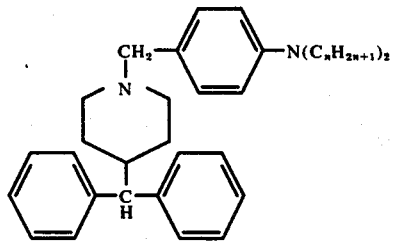

wherein $n$ represents a positive integer less than 8.

6. A compound according to claim 1 which is N,N-dimethyl-l4-{[4-(diphenylmethyl)-1-piperidinyl]-methyl}benzenamine.

* * * * *

UNITED STATES PATENT AND TRADEMARK OFFICE
CERTIFICATE OF CORRECTION

PATENT NO. : 4,035,372
DATED : July 12, 1977
INVENTOR(S) : James R. Deason, Robert W. Hamilton, Harman S. Lowrie
& Kurt J. Rorig It is certified that error appears in the above-identified patent and that said Letters Patent are hereby corrected as shown below:

Column 4, Table II, line 9, "8 $\pm$ 12" should read -- 88 $\pm$ 12 --.

Column 4, Table II, line 9, "148 $\pm$ 2.5$^+$" should read -- 14.8 $\pm$ 2.5$^+$ --.

Column 4, Table II, line 10, "2.8/160    1/4" should read -- 2.8    160    1/4 --.

Column 7, line 53 ")amino]benzoic" should read -- amino]benzoic --.

Column 8, line 66, "dimethyl-14" should read -- dimethyl-4 --.

Signed and Sealed this

*Twenty-fifth* Day of *October 1977*

[SEAL]

*Attest:*

RUTH C. MASON
*Attesting Officer*

LUTRELLE F. PARKER
*Acting Commissioner of Patents and Trademarks*